US010548514B2

(12) United States Patent
Lokshin et al.

(10) Patent No.: US 10,548,514 B2
(45) Date of Patent: Feb. 4, 2020

(54) SYSTEMS AND METHODS FOR IDENTIFYING AND CHARACTERIZING ATHLETIC MANEUVERS

(71) Applicant: AlpineReplay, Inc., Huntington Beach, CA (US)

(72) Inventors: Anatole M. Lokshin, Huntington Beach, CA (US); Vitaly A. Kuzkin, Saint Petersburg (RU)

(73) Assignee: ALPINEREPLAY, INC., Huntington Beach, CA (US)

(*) Notice: Subject to any disclaimer, the term of this patent is extended or adjusted under 35 U.S.C. 154(b) by 883 days.

(21) Appl. No.: 13/932,899

(22) Filed: Jul. 1, 2013

(65) Prior Publication Data

US 2014/0257743 A1   Sep. 11, 2014

Related U.S. Application Data

(60) Provisional application No. 61/774,050, filed on Mar. 7, 2013.

(51) Int. Cl.
*A61B 5/11* (2006.01)

(52) U.S. Cl.
CPC .................... *A61B 5/1123* (2013.01)

(58) Field of Classification Search
CPC ..... A63B 43/00; A63B 24/00; A63B 24/0003; A63B 69/36; A63B 43/008; G06F 15/00;
(Continued)

(56) References Cited

U.S. PATENT DOCUMENTS

| 4,800,897 A | 1/1989 | Nilsson |
| 5,067,717 A | 11/1991 | Harlan et al. |

(Continued)

FOREIGN PATENT DOCUMENTS

| JP | 2005286394 | 10/2005 |
| JP | 2012008683 | 1/2012 |

(Continued)

OTHER PUBLICATIONS

International Patent Application PCT/US2013/059410, International Search Report and Written Opinion, dated Dec. 9, 2013.

(Continued)

*Primary Examiner* — Regis J Betsch
*Assistant Examiner* — Kaleria Knox
(74) *Attorney, Agent, or Firm* — Greenberg Traurig, LLP

(57) ABSTRACT

Embodiments of the present disclosure help automatically identify athletic maneuvers performed by actors and/or their sports equipment using data from sensors. Among other things, various embodiments help judges and spectators of extreme sports to assess athletic maneuvers based on objective, empirical data and allow action sport participants to objectively compare tricks performed at different times and/or different locations. A computer-implemented method according to one embodiment of the present disclosure comprises receiving, by a computer system, sensor data related to motion by an actor over a time period; determining, by the computer system and based on the sensor data, a plurality of motion characteristics; and identifying, based on the plurality of motion characteristics, an athletic maneuver associated with the motion by the actor during the time period.

20 Claims, 8 Drawing Sheets

(58) Field of Classification Search
CPC ......... G06F 17/00; G01P 15/02; G08B 23/00; G01C 25/00; G06N 99/005; G09B 19/0038; A61B 5/1123
USPC .......... 702/141, 727, 104, 19; 473/570, 199, 473/223, 422, 247; 600/409; 382/168; 482/1; 340/573.1; 707/727; 706/2; 434/252; 700/90

See application file for complete search history.

(56) References Cited

U.S. PATENT DOCUMENTS

| | | | |
|---|---|---|---|
| 5,337,758 A | 8/1994 | Moore et al. | |
| 5,724,265 A * | 3/1998 | Hutchings | A43B 3/0005 235/105 |
| 6,013,007 A | 1/2000 | Root et al. | |
| 6,167,356 A | 12/2000 | Squadron et al. | |
| 6,436,052 B1 | 8/2002 | Nikolic et al. | |
| 6,499,000 B2 | 12/2002 | Flentov et al. | |
| 6,825,777 B2 | 11/2004 | Vock et al. | |
| 6,963,818 B2 | 11/2005 | Flentov et al. | |
| 7,451,056 B2 | 11/2008 | Flentov et al. | |
| 7,602,301 B1 * | 10/2009 | Stirling | A61B 5/1127 340/573.1 |
| 7,631,808 B2 | 12/2009 | Kundu et al. | |
| 7,640,135 B2 | 12/2009 | Vock et al. | |
| 7,827,000 B2 * | 11/2010 | Stirling | A61B 5/1038 702/141 |
| 7,860,666 B2 | 12/2010 | Vock et al. | |
| 7,991,565 B2 | 8/2011 | Vock et al. | |
| 8,055,469 B2 * | 11/2011 | Kulach | A63B 24/0062 702/141 |
| 8,239,146 B2 | 8/2012 | Vock et al. | |
| 8,270,670 B2 | 9/2012 | Chen et al. | |
| 8,628,453 B2 * | 1/2014 | Balakrishnan | A63B 71/0686 482/1 |
| 8,929,709 B2 | 1/2015 | Lokshin | |
| 9,001,886 B2 | 4/2015 | Labrozzi et al. | |
| 9,476,730 B2 | 10/2016 | Samarasekera et al. | |
| 9,769,387 B1 | 9/2017 | Beard et al. | |
| 10,008,237 B2 | 6/2018 | Lokshin et al. | |
| 10,212,325 B2 | 2/2019 | Lokshin et al. | |
| 10,213,137 B2 | 2/2019 | Lokshin et al. | |
| 10,321,208 B2 | 6/2019 | Lokshin et al. | |
| 10,408,857 B2 | 9/2019 | Lokshin et al. | |
| 2002/0115927 A1 * | 8/2002 | Tsukada | A61B 5/04005 600/409 |
| 2004/0225467 A1 | 11/2004 | Vock et al. | |
| 2006/0166737 A1 | 7/2006 | Bentley | |
| 2006/0190419 A1 * | 8/2006 | Bunn | G06N 99/005 706/2 |
| 2008/0096726 A1 | 4/2008 | Riley et al. | |
| 2009/0088204 A1 | 4/2009 | Culbert et al. | |
| 2009/0210078 A1 * | 8/2009 | Crowley | G06Q 30/02 700/91 |
| 2010/0081116 A1 * | 4/2010 | Barasch | A63B 24/0003 434/252 |
| 2010/0113115 A1 | 5/2010 | Hightower | |
| 2010/0191499 A1 | 7/2010 | Vock et al. | |
| 2010/0268459 A1 | 10/2010 | O'Shea | |
| 2011/0007962 A1 | 1/2011 | Johnson et al. | |
| 2011/0210915 A1 * | 9/2011 | Shotton | G06K 9/00369 345/157 |
| 2011/0222766 A1 * | 9/2011 | Kato | G06K 9/481 382/168 |
| 2011/0246122 A1 * | 10/2011 | Iketani | G01P 13/00 702/141 |
| 2012/0004883 A1 | 1/2012 | Ikeda et al. | |
| 2012/0116548 A1 * | 5/2012 | Goree | A61B 5/1118 700/90 |
| 2012/0154557 A1 | 6/2012 | Perez et al. | |
| 2012/0191705 A1 * | 7/2012 | Tong | G06F 17/30864 707/727 |
| 2012/0251079 A1 | 10/2012 | Meschter et al. | |
| 2012/0264549 A1 * | 10/2012 | Homsi | A63B 43/008 473/422 |
| 2013/0041590 A1 * | 2/2013 | Burich | G06F 19/3418 702/19 |
| 2013/0188067 A1 | 7/2013 | Koivukangas et al. | |
| 2013/0218504 A1 * | 8/2013 | Fall | G01C 25/00 702/104 |
| 2013/0242105 A1 | 9/2013 | Boyle et al. | |
| 2013/0265440 A1 | 10/2013 | Mizuta | |
| 2013/0274040 A1 * | 10/2013 | Coza | G09B 19/0038 473/570 |
| 2013/0302768 A1 * | 11/2013 | Webb | G09B 19/0038 434/247 |
| 2013/0316840 A1 * | 11/2013 | Marks | G09B 19/0038 473/199 |
| 2013/0330054 A1 | 12/2013 | Lokshin | |
| 2014/0028855 A1 | 1/2014 | Pryor | |
| 2014/0257744 A1 | 9/2014 | Lokshin et al. | |
| 2014/0287389 A1 | 9/2014 | Kallmann et al. | |
| 2015/0050972 A1 | 2/2015 | Sarrafzadeh et al. | |
| 2015/0154452 A1 | 6/2015 | Bentley et al. | |
| 2015/0335949 A1 | 11/2015 | Lokshin et al. | |
| 2015/0340066 A1 | 11/2015 | Lokshin et al. | |
| 2016/0006974 A1 | 1/2016 | Pulkkinen et al. | |
| 2016/0045785 A1 | 2/2016 | Tzovanis et al. | |
| 2016/0225410 A1 | 8/2016 | Lee et al. | |
| 2016/0241768 A1 | 8/2016 | Lokshin et al. | |
| 2019/0182417 A1 | 6/2019 | Lokshin et al. | |
| 2019/0261065 A1 | 8/2019 | Lokshin et al. | |

FOREIGN PATENT DOCUMENTS

| | | |
|---|---|---|
| JP | 2012523900 | 10/2012 |
| JP | 2013130808 | 7/2013 |
| WO | 2014073454 | 5/2014 |

OTHER PUBLICATIONS

European Patent Application No. 13877362.7, Supplementary Search Report, dated Sep. 29, 2016.
Tsai, A Versatile Camera Calibration Techniaue for High-Accuracy 3D Machine Vision Metrology Using Off-the-shelf TV Cameras and Lenses, IEEE Journal of Robotics and Automation, vol. RA-3, No. 4, Aug. 1987, pp. 323-344.
International Patent Application PCT/US2015/047251, International Search Report and Written Opinion, dated Dec. 16, 2015.
International Patent Application No. PCT/US2016/018291, International Search Report and Written Opinion, dated Apr. 26, 2016.

* cited by examiner

SYSTEMS AND METHODS FOR IDENTIFYING AND CHARACTERIZING ATHLETIC MANEUVERS

CROSS-REFERENCE TO RELATED APPLICATION

This application claims priority to U.S. Provisional Patent Application No. 61/774,050, filed Mar. 7, 2013 and entitled "METHOD AND APPARATUS FOR MEASURING ACTION SPORT TRICKS," the content of which is incorporated by reference in its entirety.

This application relates to U.S. patent application Ser. No. 13/612,470, filed Sep. 12, 2012 and entitled "METHOD AND APPARATUS FOR DETERMINING SPORTSMAN JUMPS USING FUZZY LOGIC", the disclosure of which application is hereby incorporated herein by reference.

BACKGROUND

The popularity of extreme sports (also referred to as "action sports" or "adventure sports") is steadily growing. In particular, sports such as snowboarding, skateboarding, free skiing, surfboarding, skydiving, wingsuit flying, bicycle motocross (BMX), and others are becoming (or are currently) mainstream sports. Such sports are increasingly being covered by various media organizations and some competitions (such as the X-Games) are devoted solely to extreme sports.

In many traditional sports, competitions are measured and judged using objective measures such as scores (e.g., the number of runs in a baseball game or points in a basketball game) or times (e.g., the time for a runner or downhill skier to cross a finish line). In many extreme sports, by contrast, athletes compete by performing various athletic maneuvers (or "tricks") such as jumps, flips, rotations, and the like. As an example, a description of common tricks that are performed in snowboarding can be found at http://en.wikipedia.org/wiki/List_of_snowboard_tricks and a description of common skateboarding tricks at http://skateboardingtrickslist.com.

Many athletic maneuvers in extreme sports are complex and/or performed very quickly. Accordingly, athletic maneuvers performed in action sports competitions are often evaluated (by judges and spectators) based on a variety of subjective factors, including an individual's personal perception of the difficulty or aesthetics of a particular athletic maneuver. This often leads to problems in identifying different athletic maneuvers, as well as judging or rating such maneuvers in competition. In ski jump competitions, for example, the movement of the jumper may be so fast that spectators cannot determine the number of rotations or flips the jumper performs.

Some conventional systems attempt to measure fast rotations with inertial sensors. Such measurements are typically made relative to the sensor axis but can be related to the absolute axis as well. However, such conventional systems do not make sensor measurements understandable to the sport participants and spectators. Conventional systems are unable to automatically recognize and measure action sport "tricks," and are thus unsuitable for virtual competitions, leaderboards, and social networks dedicated to the action sport participants. Embodiments of the present disclosure address these and other issues.

SUMMARY OF THE DESCRIPTION

Embodiments of the present disclosure help identify athletic maneuvers performed by actors and/or their sports equipment using data from sensors. Among other things, various embodiments help judges and spectators of extreme sports to assess athletic maneuvers based on objective, empirical data.

A computer-implemented method according to one embodiment of the present disclosure comprises receiving, by a computer system, sensor data related to motion by an actor over a time period; determining, by the computer system and based on the sensor data, a plurality of motion characteristics; and identifying, based on the plurality of motion characteristics, an athletic maneuver associated with the motion by the actor during the time period.

Another embodiment of the present disclosure includes means for receiving sensor data related to motion by an actor over a time period; determining, based on the sensor data, a plurality of motion characteristics; and identifying, based on the plurality of motion characteristics, an athletic maneuver associated with the motion by the actor during the time period.

The present disclosure includes methods and apparatuses which perform these methods, including data processing systems which perform these methods, and computer readable media containing instructions which when executed on data processing systems cause the systems to perform these methods.

Other features will be apparent from the accompanying drawings and from the detailed description which follows.

BRIEF DESCRIPTION OF THE DRAWINGS

A more complete understanding of certain embodiments may be derived by referring to the detailed description and claims when considered in connection with the following illustrative figures.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Any combination and/or subset of the elements of the methods depicted herein may be practiced in any suitable order and in conjunction with any suitable system, device, and/or process. The methods described and depicted herein can be implemented in any suitable manner, such as through software operating on one or more computer systems. The software may comprise computer-readable instructions stored in a tangible computer-readable medium (such as the memory of a computer system) and can be executed by one or more processors to perform the methods of various embodiments.

Figure 1:
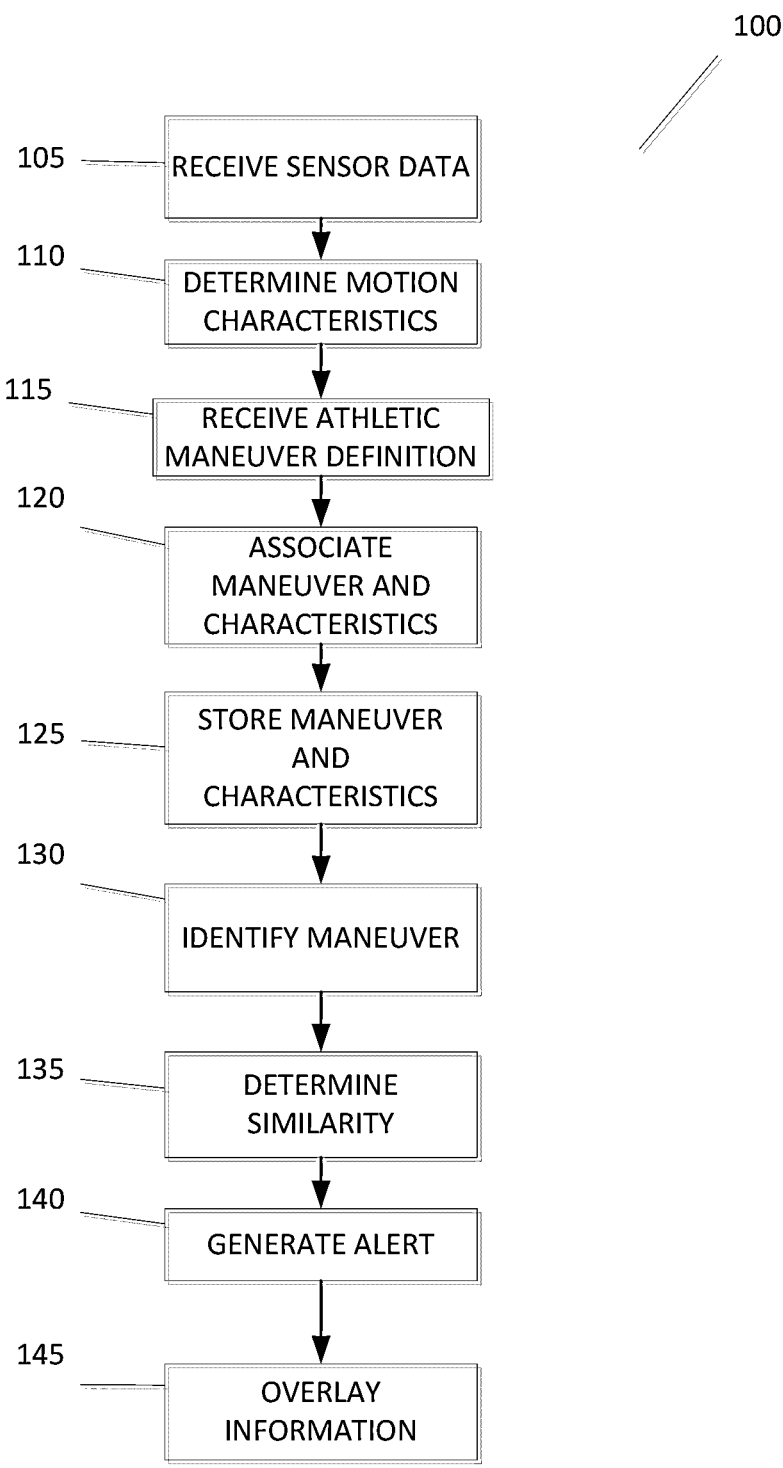
FIGS. 1 and 1A are flow diagrams showing exemplary processes according to various embodiments.

FIG. 1 depicts an exemplary process according to various embodiments of the present disclosure. In FIG. 1, method 100 includes receiving sensor data (105) related to motion by an actor over a period of time and determining motion characteristics based on the sensor data (110). Method 100 further includes receiving input related to a definition of an athletic maneuver (115), associating one or more motion characteristics with the definition (120), and storing the athletic maneuver definition and associated motion characteristics in a database (125). Method 100 further includes identifying one or more athletic maneuvers based on the determined motion characteristics (130), determining a level of similarity between the determined motion characteristics and motion characteristics associated with the identified athletic maneuver(s) (135), and generating an alert (140) in response to the similarity level being below a predetermined threshold. Method 100 also includes combining or overlaying information related to the athletic maneuver with video of the athletic maneuver (145). The steps of method 100 may be implemented (in whole or in part, and in any desired order) by software operating on a computer system, such as the exemplary computer system 200 depicted in FIG. 2.

Embodiments of the present disclosure may receive sensor data (105) directly or indirectly from any number and type of sensors, such as an accelerometer, a gyroscope, a magnetometer, a Hall effect sensor, a global positioning system, an ultrasonic sensor, an optical sensor; and combinations thereof. Information from different sensors may be used together or separately to determine various motion characteristics for the actor and/or the actor's equipment. As used in this context, an "actor" performing an athletic maneuver may refer to any human (e.g., skier, snowboarder, cyclist, diver, athlete, etc.) as well as to sporting equipment associated with, or controlled by, a human. Such sporting equipment may include, for example, a vehicle (such as a bicycle, boat, automobile, motorcycle, etc.), a skateboard, skis, a snowboard, a parachute, and other equipment or devices.

Figure 7:
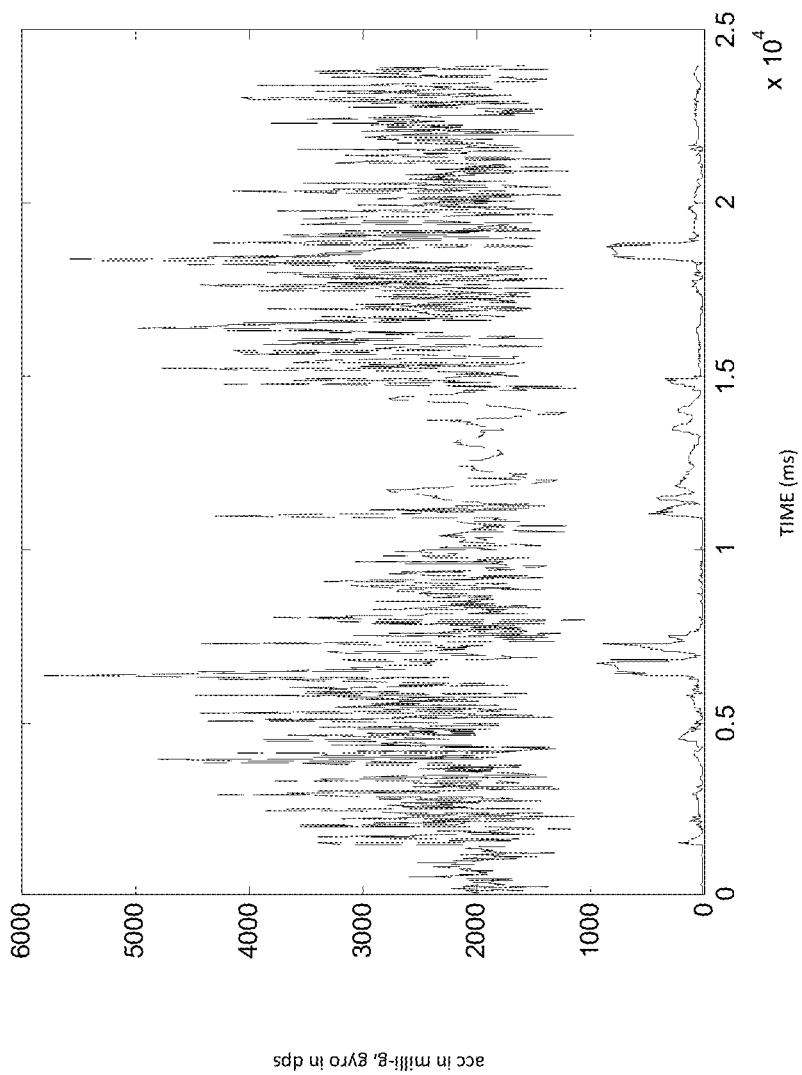

For example, Hall effect sensors may be used to monitor the speed of a stunt bicyclist's wheels before, during, and after a jump, while data from one set of accelerometers and gyroscopes can monitor flips and rotations performed by the bicyclist and a second set of accelerometers and gyroscopes can monitor flips and rotations of the bicycle itself. Other sensors, such as an optical sensor (e.g., a proximity sensor) or global positioning system can be used to help determine actor's position with regards to the ground, ramp, other actors, and other objects. Various embodiments may utilize data from sensors imbedded in or attached to an actor's clothing, skin, equipment, or surroundings (e.g., in a ramp used by an actor to perform jumps). The sensor data may be received in any suitable manner, such as wirelessly from a data collection system coupled to an actor and/or an actor's equipment. The time interval when a maneuver or "trick" is performed can be determined by identifying and measuring a jump by monitoring and analyzing characteristic signature of the gyro sensors using fuzzy logic as described in U.S. patent application Ser. No. 13/612,470, the contents of which are incorporated by reference herein. For example, FIG. 7 compares a signal from accelerometers and gyro sensors recorded by a device that was attached to a skateboard during maneuvers performed by a skateboarder. To aid in separating the signals, the accelerometer norm was shifted up by 1000 mili-g. FIG. 7 shows that while accelerometer signal is very noisy due to the board vibration, the gyro signal is much better correlated with the trick time period.

Embodiments of the present disclosure can be particularly effective in identifying and characterizing athletic maneuvers for extreme sports based on objective data. Additionally, various embodiments may be used in conjunction with various other sports and activities, such as baseball, basketball, hockey, soccer, and football. For example, embodiments of the present disclosure may be configured to receive data from sensors coupled to a baseball player's bat, as well as from sensors attached to the player's uniform and/or embedded in a baseball. In one such embodiment, information regarding a player hitting a baseball, such as the angle of the player's swing, the velocity of the bat, and the force at which the baseball is hit can be provided to various users, such as spectators of a baseball game or trainers seeking to optimize the player's swing. As discussed in more detail below, such information can be provided in conjunction with video of the player hitting the ball, either in near-real-time as the video is broadcast to spectators, as well as part of a replay of the hit. In this manner, embodiments of the present disclosure can provide information to enhance a spectator's experience (e.g., displaying the force applied to a baseball from a 420-foot home run) as well as to help players, trainers, and coaches improve an athlete's performance based on objective information.

Any number of different motion characteristics may be determined (110). The motion characteristics may include any desired information regarding the motion of an actor or equipment used by an actor, such as position, velocity, acceleration, orientation, rotation, translation, and changes to and combinations thereof. Embodiments of the present disclosure can determine multiple motion characteristics during a period of time that includes an athletic maneuver performed by an actor. For example, the orientation of a snowboarder executing a complex series of flips and rotations during jump can be monitored at various points or times (e.g., each millisecond) within a time period starting prior to the jump and ending after the jump.

Motion characteristics may include any number of different values, descriptions, and other information characterizing the movement (or lack thereof) of an actor and/or the actor's equipment. For example, a motion characteristic associated with an athletic maneuver may include one or more of: an orientation of the actor at a time within the time period (e.g., prior to, during, or after a maneuver), an angle of rotation around a local axis of the actor, a direction of rotation of the actor around a local axis of the actor, an angle of rotation around an absolute axis perpendicular to a plane of motion of the actor, a direction of rotation round an absolute axis perpendicular to a plane of motion of the actor, and combinations thereof.

Motion characteristics may be determined in any suitable manner. For example, motion characteristics can be determined based on two different frames of reference: an absolute frame of reference that is independent of the actor and independent of the actor's motion, and a local frame of reference that is associated with (i.e., connected to, and moves with) the actor. Embodiments of the present disclosure can characterize and measure a variety of different athletic maneuvers based on analyzing a combination of motion characteristics measured relative to the absolute and local frames of reference.

Embodiments of the present disclosure may also utilize information regarding the placement or location of various sensors in determining various motion characteristics. For example, determining rotation about an axis along the actor's body may be based on sensors (e.g., accelerometers and gyroscopes) being positioned collinearly with each other, such that sensors along one of the three-dimensional axes (x, y, and z) are the same. Embodiments of the present disclosure may also utilize calibration information from the sensors, such as calibration of various sensors performed during manufacturing of the sensors or installation of the sensors in an actor's clothing, equipment, etc. Various embodiments of the present disclosure may also be configured to communicate with various sensors (or control systems coupled thereto) to calibrate the sensors. Such calibration may be performed in any suitable manner. In one embodiment, for example, calibration of one or more inertial sensors attached to an actor and/or the actor's equipment can be calibrated when the sensors indicate the actor and/or equipment is not moving.

While multiple sensors may provide a large amount of information about an actor's motion, and the motion itself can be expressed by Euler angles, pitch, roll, and yaw, or rotational matrix, this information is understood by the participants, judges, and spectators only if it is expressed in the terms and sport-specific nomenclature that is commonly accepted in the sport performed by the actor. Embodiments of the present disclosure translate sensor observations to identify "tricks" using such nomenclature. Embodiments of the present disclosure can identify key motions for each trick, detect and measure all such motions, and then identify a trick and its quality or level of difficulty by comparing the detected motions with the nominal motions required for each trick.

While not exhaustive, the most common characteristics that define different tricks are: the orientation of the actor prior to the trick (forward facing, backward facing, left side facing, right side facing), the leading edge of the trick (e.g., starting from the front or end of the user's board), rotation around an absolute axis that is horizontal and perpendicular to the direction of motion during the trick (flip axis), and rotation around an axis associated with the body of the actor (self rotation axis). In characterizing a trick, a rotation angle around any axis does not have to be a full rotation but could be a "back and forth" swing at some particular angle, (e.g., a "Shifty" trick).

In various embodiments, determining the orientation of an actor (or the actor's equipment) at various points during a time period includes determining an angle of self-rotation for the actor and determining an angle of flip for the actor. For example, an actor (such as a skateboarder) performing a jump may be monitored using three gyroscopes and three accelerometers connected to the actor's equipment, body, or clothing. For this example, it is assumed that all the sensors are positioned in a device such that their local axes are collinear as described above. The orientation of the actor at time t with respect to a fixed reference frame is determined by a quaternion L(t). The quaternion change satisfies the following kinematic equation:

$$L\_dot = \frac{1}{2} \omega^\circ L, \quad \text{(Equation 1)}$$

In Equation 1, L_dot is a time derivative of L(t), $\omega$ is angular velocity of the body, measured by (for example) the gyroscopic sensors. As an initial condition, L(0) (i.e., the orientation of the actor before the jump) can be determined. Alternatively, the orientation of the actor immediately after the jump can be determined, namely L(t_max) where t_max is a time after the actor lands. The orientation of the actor (including the actor's facing/orientation prior to, or after, a maneuver) can be determined in any desired manner, such as based on a direction of a velocity vector calculated from the sensor data (e.g., from a GPS sensor) and the orientation of the actor calculated from other sensor data (e.g., from a magnetometer).

In a practical system, determining L(t_max) may be preferable where a landing shock (i.e., a large acceleration after the jump) in the opposite directed with respect to gravity is measurable. Given the orientation of the actor after the jump, the equation thus becomes:

$$L(t\_max) \approx [\cos \varphi/2; e \sin \varphi/2];$$

$$e = (g \times a\_shock)/(|g \cdot a\_shock|); \text{ and}$$

$$\varphi = a \cos((g \cdot a\_shock)/\|g\| \|a\_shock\|).$$

Here, "≈" means that there may be some error associated with the final quaternion L(t_max), however this approximation may still be sufficient from practical point of view where the absolute orientation of the sportsman is not needed for calculation of turns during the jump.

Given the orientation at the end of the jump, L(t_max), the equations may be reformulated in classical Cauchy form (ODE with initial conditions), and using the new variable τ:

$$t = t\max - \tau.$$

Substituting the given expression into Equation 1 obtains:

$$d/dt\, L = -d/d\tau\, L = \frac{1}{2} \omega(t\max - \tau)^\circ L(t\max - \tau).$$

Thus orientation of the sportsman can be determined solving the following Cauchy problem:

$$(d/d\tau L\tilde{}(\tau) = -\frac{1}{2} \omega\tilde{}(\tau)^\circ L\tilde{}(\tau)$$

$$\tau \in [0; t\max];$$

$$\tilde{L}(\tau) \stackrel{def}{=} L(t\max - \tau); \text{ and}$$

$$\omega(\tau) \stackrel{def}{=} \tilde{\omega}(t\max - \tau))$$

Figure 3:
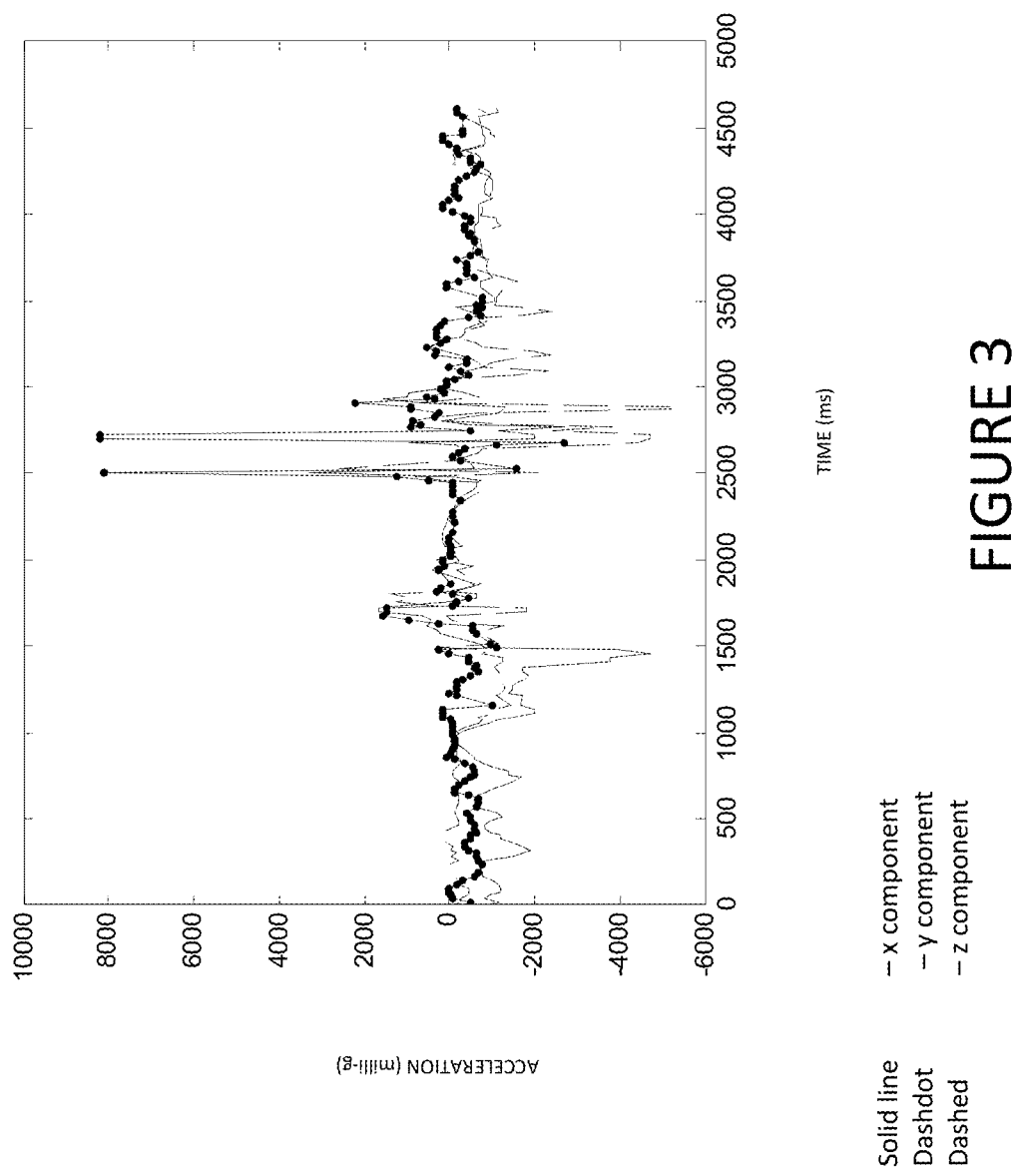
FIGS. 3, 4, 5, 6A, 6B, and 7 are exemplary graphs according to various aspects of the present disclosure.

In this example, a local vertical axis may be determined to (for example) calculate an angle of self-rotation of the actor during the jump. A local vertical axis may be determined in a variety of different ways, including based on an average of sensor data from one or more accelerometers prior to the athletic maneuver, an average of sensor data from one or more accelerometers after the athletic maneuver, sensor data from one or more accelerometers associated with a portion of the athletic maneuver (such as a landing performed after the maneuver), sensor data from one or more magnetometers (e.g., in conjunction with the nominal orientation of a magnetic vector relative to the vertical at the location of the event), and combinations thereof. FIG. 3 depicts an exemplary graph of sensor data measured from three accelerometers that shows the shock of an impact from an actor landing after a jump. In this graph, the horizontal graph axis depicts time in milliseconds and the vertical axis depicts acceleration in m/s^2. The three accelerometers correspond to acceleration in the x, y, and z planes.

The angle of self-rotation for the actor may be determined in any suitable manner, including by calculating a path for each of a plurality of unit vectors in a local frame of reference that is associated with the actor, the plurality of unit vectors being orthogonal to a local vertical vector for the actor. The angle of self-rotation for the actor may then be selected as the largest rotation angle among such unit vectors.

Likewise, the angle of flip for the actor may be calculated in any desired manner, including by determining the motion of a vertical vector in a global frame of reference that is associated with the actor, identifying a plane of movement for the unit vertical vector, calculating a projection of the vertical vector on the plane, and selecting the angle of flip for the actor as the angle of the arc traveled by such projection on the plane.

Figure 4:
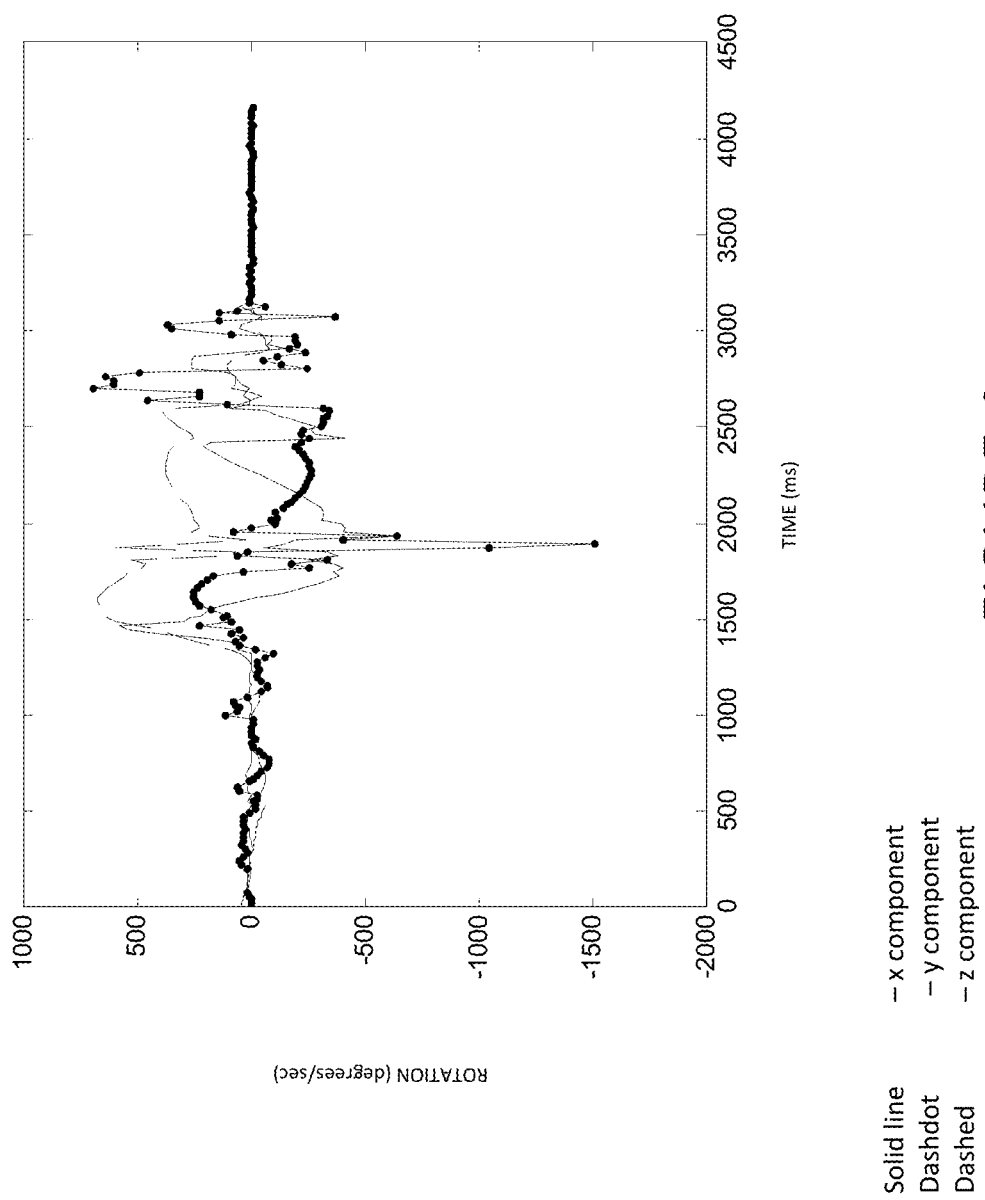

FIG. 4 is an exemplary graph depicting self-rotation over time. In this example, sensor data from three gyroscopic sensors (corresponding to the x, y, and z planes as in FIG. 3) rotated around a nearly vertical axis in a nearly horizontal plane is plotted over time. In this graph, the vertical axis depicts rotation speed in rad/sec. Using the algorithms described above, the angle of self-rotation calculated for this data is about 363 degrees, and the angle of flip is calculated at less than 1 degree.

Figure 5:
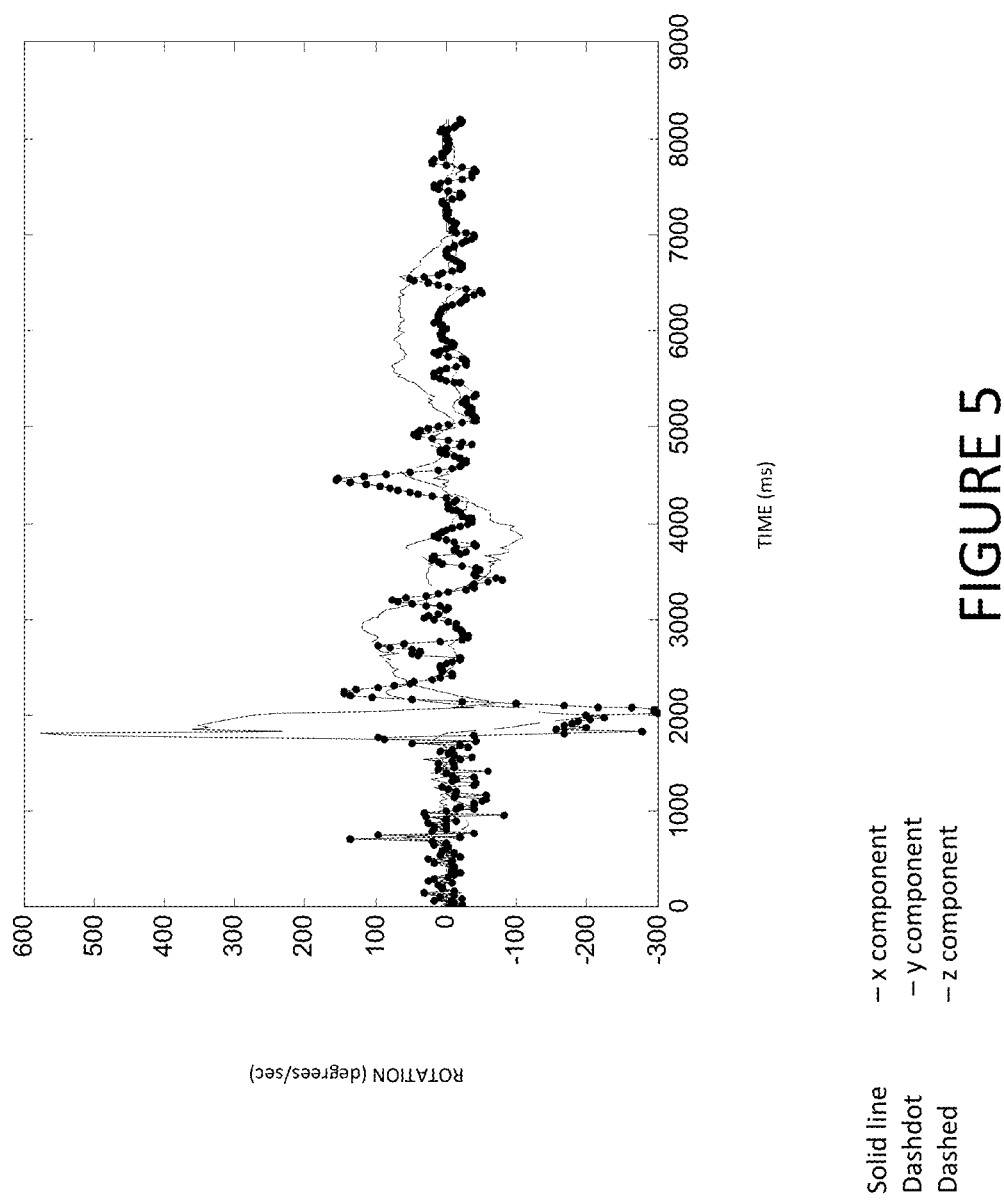
Figure 6B:
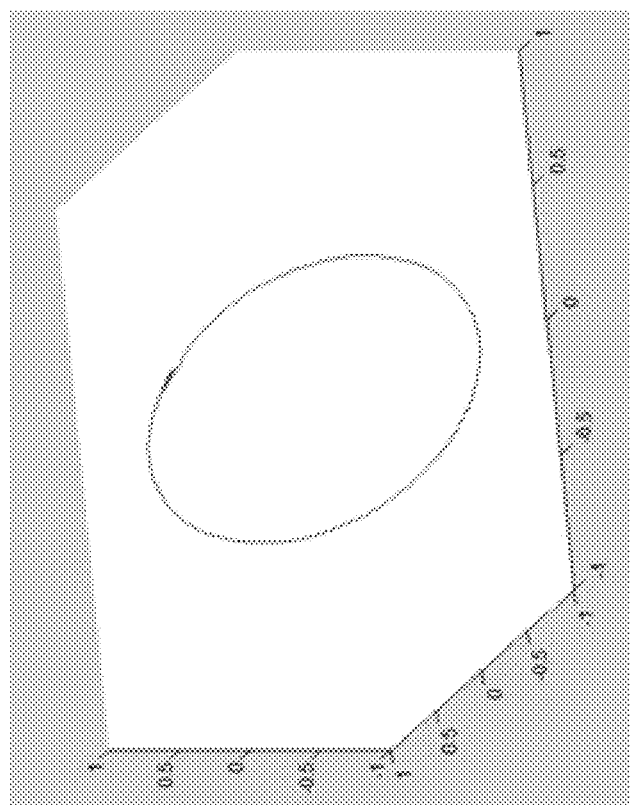
Figure 6A:
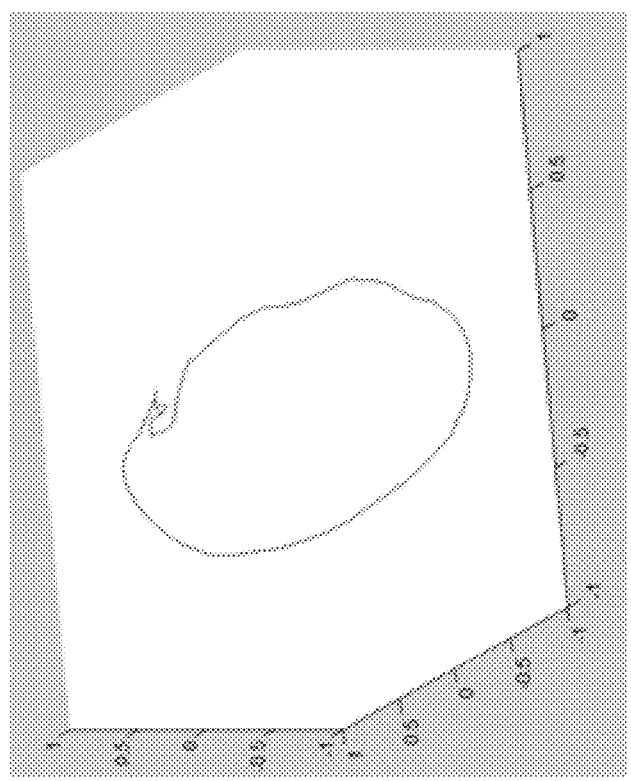

FIG. 5 is an exemplary graph depicting an angle of flip over time. In this example, sensor data from a gyroscopic sensor flipped (i.e., rotated about a nearly horizontal axis) is plotted over time (in milliseconds). FIG. 6A depicts the trajectory of the vector connected with the sensor that coincides with the vertical vector at the end of the rotation, while FIG. 6B depicts the projection of the trajectory on the plane of rotation (nearly round in this example). The resulting angle of flip rotation is about 358 degrees and the angle of self-rotation is about 38 degrees in this example.

Definitions for any desired athletic maneuvers can be received (115), associated with one or more motion characteristics (120), and stored in a database for future reference and retrieval (125). A definition for an athletic maneuver may apply to any movement or group of movements by an actor, the actor's equipment, or a combination thereof. For example, a back flip combined with a side flip performed by a snowboarder is often referred to as a "wildcat." A definition for a wildcat maneuver may thus include the name (or aliases) of the maneuver, a textual description of the maneuver, and the motion characteristic(s) associated with the maneuver. Continuing this example, the motion characteristics associated with the wildcat may include indicators of the different axes of rotation by the actor's body and the rotation angles around these axes. Other information, such as a typical range of forces exerted on the actor's snowboard or parts of the actor's body and a range of time the snowboarder is airborne may be associated with the definition to help identify future wildcat jumps by comparing measured motion characteristics to the wildcat jump definition in the database.

The definition for an athletic maneuver may include any number of complex movements by an actor and/or the actor's equipment. For example, sensor data from sensors attached to the actor (such as a skateboarder) can be analyzed in conjunction with sensor data from the actor's equipment (such as a skateboarder). In this manner, rotations, flips, and other movement by the actor can be analyzed together with rotations and flips of the skateboard to identify all movements performed by the actor and provide a complete and accurate characterization of the maneuver performed. Embodiments of the present disclosure can thus be particularly effective in characterizing and identifying maneuvers that are complex and/or fast, therefore making it challenging for spectators and judges to identify all the movements involved.

A definition for an athletic maneuver may include, or be associated with, any other desired information. For example, statistics (including motion characteristics) for particular athletes who perform a maneuver may be linked to the definition of the maneuver in a database, allowing users of the systems and methods of the present disclosure to compare the manner in which various athletes perform the maneuver. Other information, such as video of the maneuver being performed, may likewise be included in, or linked to, the definition.

One or more determined motion characteristics can be compared to the motion characteristics associated with a known athletic maneuvers in a database to identify the maneuver (130) associated with the determined motion characteristics. The motion characteristics determined for an unknown maneuver may be compared to motion characteristics for known maneuvers in any suitable manner. For example, characteristics describing an actor's velocity, angle of self-rotation, angle of flip, and change in orientation during a time period can be compared to a relational database storing motion characteristics associated with the known maneuvers. Known motion characteristics in the database may be represented in nominal values and/or in ranges, reflecting that different actors may have different physical characteristics (e.g., height, weight), may have different equipment, may perform the same maneuver somewhat differently, and/or may perform a maneuver under various other conditions (e.g., with different types of ramps).

The database may also specify the quality of the maneuver that is associated with different parameter values. For example, a full rotation of 360 degrees during a jump may be valued in 10 points, while a partial rotation of only 350 dg (from jump start to landing) may be valued only at 9 points. The quality of a maneuver may be determined according to any desired factors, such as the difficulty of the maneuver.

A level of similarity between a determined set of motion characteristics and a known nominal set of motion characteristics may be determined (135). The level of similarity may be determined for each of a plurality of motion characteristics. Alternatively (or in addition), an overall level of similarity may be determined for an entire maneuver. The level(s) of similarity may be compared to various threshold values, and an alert generated if one or more similarity levels fail to meet a threshold value. In this manner, embodiments of the present disclosure can identify new (i.e., undefined) maneuvers and help administrators and users of the systems and methods described herein to identify errors in the values or associations of stored motion characteristics and modify them appropriately.

Figure 1A:
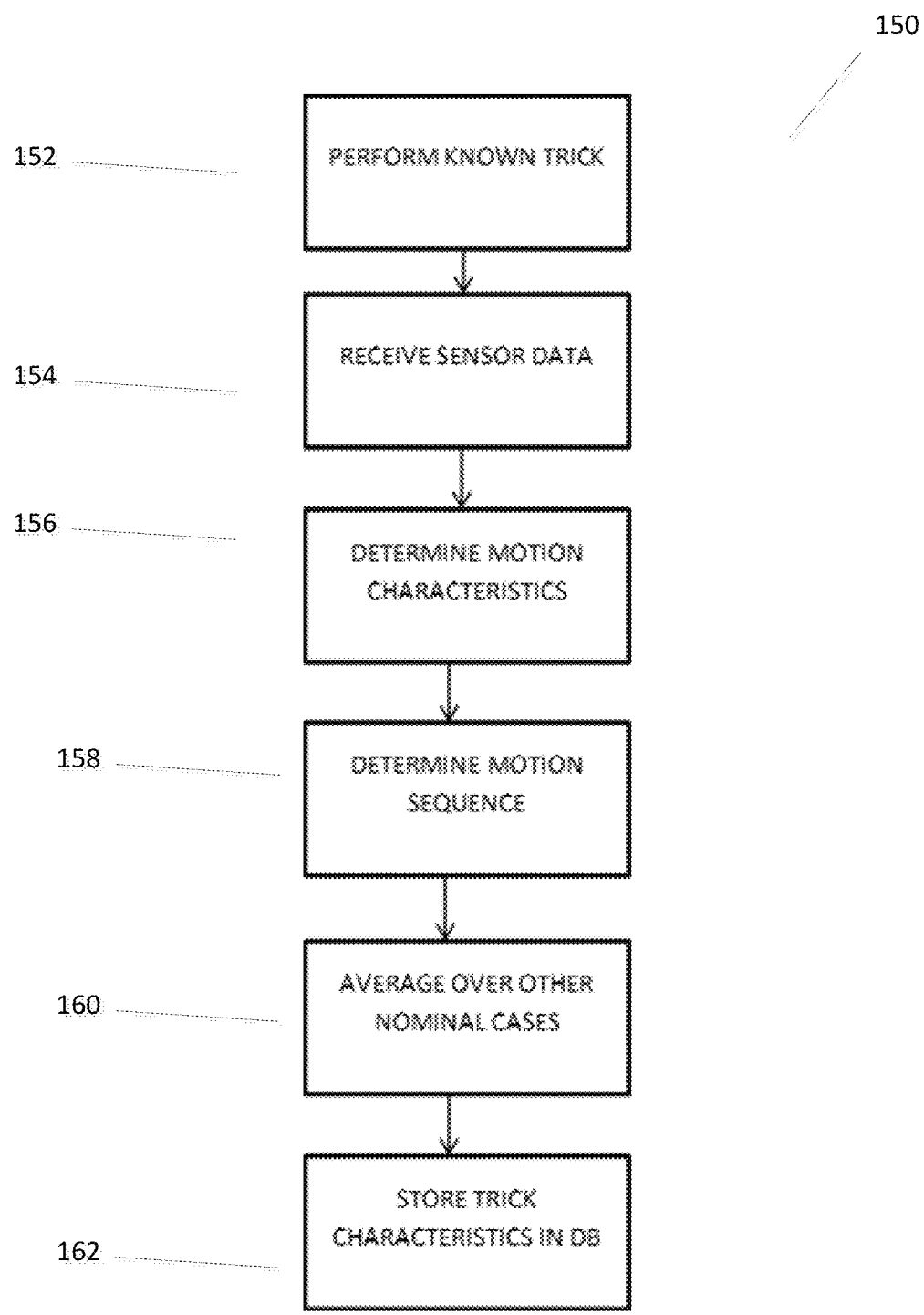

FIG. 1A depicts an exemplary method for populating a database with information regarding various athletic maneuvers. In this example, method 150 includes receiving sensor data (154) from a performed trick (152), and determining motion characteristics (156) and motion sequences (158) based on the received data. The motion characteristics and/or motion sequences may be averaged over other nominal cases (160) of the same trick, and a set of trick characteristics stored in the database (162).

Embodiments of the present disclosure may combine or overlay information identified and/or measured for an athletic maneuver (145) with any desired form of media. For example, information regarding an athletic maneuver can be combined or overlaid onto video taken of the athletic maneuver, thus providing near-real-time information on a maneuver to spectators or judges. Such an overlay can be synchronized in any desired manner, including by using a time measured from a global positioning system or other sensor operating in conjunction with embodiments of the present disclosure.

Embodiments of the disclosure may also be configured to automatically generate and transmit reports, statistics, and/or analyses based on information related to various athletic maneuvers. These may be provided in real-time or near-real-time to judges, spectators, social media outlets, broadcasting entities, websites, and other systems and entities.

Figure 2:
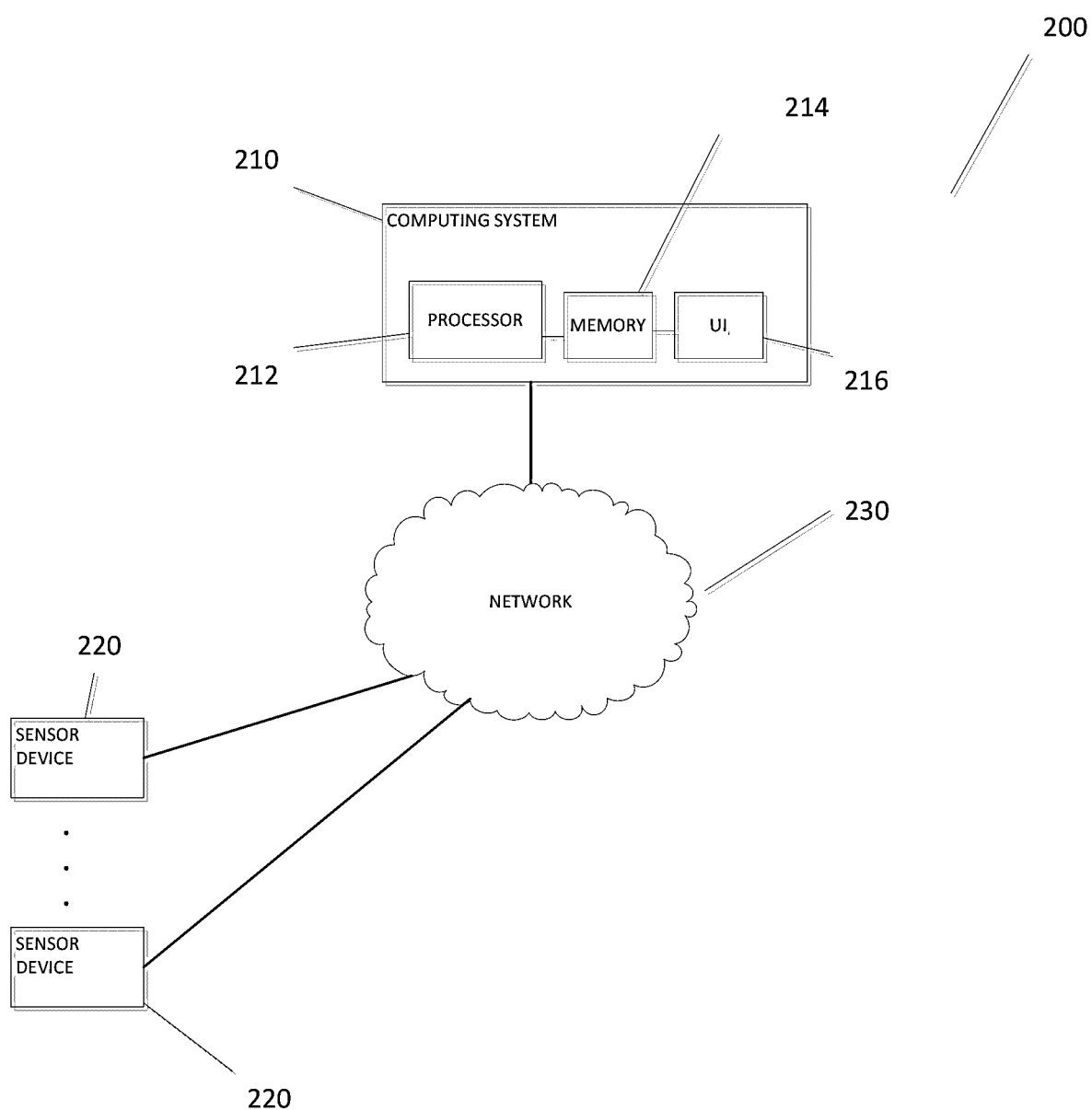
FIG. 2 is a block diagram of an exemplary system according to various embodiments.

FIG. 2 is a block diagram of system which may be used in conjunction with various embodiments. While FIG. 2 illustrates various components of a computer system, it is not intended to represent any particular architecture or manner of interconnecting the components. Other systems that have fewer or more components may also be used.

In FIG. 2, the system 200 includes a computer system 210 comprising a processor 212, memory 214, and user interface 216. Computer system 210 may include any number of different processors, memory components, and user interface components, and may interact with any other desired systems and devices in conjunction with embodiments of the present disclosure.

The functionality of the computer system 210, including the method depicted in FIG. 1, (in whole or in part), may be implemented through the processor 212 executing computer-readable instructions stored in the memory 214 of the system 210. The memory 214 may store any computer-readable instructions and data, including software applications, applets, and embedded operating code.

The functionality of the system 210 or other system and devices operating in conjunction with embodiments of the present disclosure may also be implemented through various hardware components storing machine-readable instructions, such as application-specific integrated circuits (ASICs), field-programmable gate arrays (FPGAs) and/or complex programmable logic devices (CPLDs). Systems according to aspects of certain embodiments may operate in conjunction with any desired combination of software and/or hardware components. The processor 212 retrieves and executes instructions stored in the memory 214 to control the operation of the system 210. Any type of processor, such as an integrated circuit microprocessor, microcontroller, and/or digital signal processor (DSP), can be used in conjunction with embodiments of the present disclosure. A memory 214 operating in conjunction with embodiments of the disclosure may include any combination of different memory storage devices, such as hard drives, random access memory (RAM), read only memory (ROM), FLASH memory, or any other type of volatile and/or nonvolatile memory. Data (such as athletic maneuver definitions and associated motion characteristics) can be stored in the memory 214 in any desired manner, such as in a relational database.

The system 210 includes a user interface 216 may include any number of input devices (not shown) to receive commands, data, and other suitable input from a user such as input regarding the definitions of athletic maneuvers. The user interface 216 may also include any number of output devices (not shown) to provides the user with data, notifications, and other information. Typical I/O devices may include mice, keyboards, modems, network interfaces, printers, scanners, video cameras and other devices.

The system 210 may communicate with one or more sensor devices 220, as well as other systems and devices in any desired manner, including via network 230. The sensor devices 220 may include, or be coupled to, one or more control systems (not shown) through which the system 210 communicates with, or the system 210 may communicate directly with the sensors 220.

The system 210 may be, include, or operate in conjunction with, a laptop computer, a desktop computer, a mobile subscriber communication device, a mobile phone, a personal digital assistant (PDA), a tablet computer, an electronic book or book reader, a digital camera, a video camera, a video game console, and/or any other suitable computing device.

The network 230 may include any electronic communications system or method. Communication among components operating in conjunction with embodiments of the present disclosure may be performed using any suitable communication method, such as, for example, a telephone network, an extranet, an intranet, the Internet, point of interaction device (point of sale device, personal digital assistant (e.g., iPhone®, Palm Pilot®, Blackberry®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Systems and devices of the present disclosure may utilize TCP/IP communications protocols as well as IPX, Appletalk, IP-6, NetBIOS, OSI, any tunneling protocol (e.g. IPsec, SSH), or any number of existing or future protocols.

While some embodiments can be implemented in fully functioning computers and computer systems, various embodiments are capable of being distributed as a computing product in a variety of forms and are capable of being applied regardless of the particular type of machine or computer-readable media used to actually effect the distribution.

A machine readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others. The computer-readable media may store the instructions.

In various embodiments, hardwired circuitry may be used in combination with software instructions to implement the techniques. Thus, the techniques are neither limited to any specific combination of hardware circuitry and software nor to any particular source for the instructions executed by the data processing system.

Although some of the drawings illustrate a number of operations in a particular order, operations which are not order dependent may be reordered and other operations may be combined or broken out. While some reordering or other groupings are specifically mentioned, others will be apparent to those of ordinary skill in the art and so do not present an exhaustive list of alternatives. Moreover, it should be recognized that the stages could be implemented in hardware, firmware, software or any combination thereof.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: shipping data, package data, and/or any data useful in the operation of the system.

Various functionality may be performed via a web browser and/or application interfacing utilizing a web browser. Such browser applications may comprise Internet browsing software installed within a computing unit or a system to perform various functions. These computing units or systems may take the form of a computer or set of computers, and any type of computing device or systems may be used, including laptops, notebooks, tablets, hand held computers, personal digital assistants, set-top boxes, workstations, computer-servers, main frame computers, mini-computers, PC servers, network sets of computers, personal computers and tablet computers, such as iPads, iMACs, and MacBooks, kiosks, terminals, point of sale (POS) devices and/or terminals, televisions, or any other device capable of receiving data over a network. Various embodiments may utilize Microsoft Internet Explorer, Mozilla Firefox, Google Chrome, Apple Safari, Opera, or any other of the myriad software packages available for browsing the internet.

Various embodiments may operate in conjunction with any suitable operating system (e.g., Windows NT, 95/98/2000/CE/Mobile/, Windows 7/8, OS2, UNIX, Linux, Solaris, MacOS, PalmOS, etc.) as well as various conventional support software and drivers typically associated with computers. Various embodiments may include any suitable personal computer, network computer, workstation, personal digital assistant, cellular phone, smart phone, minicomputer, mainframe or the like. Embodiments may implement security protocols, such as Secure Sockets Layer (SSL), Transport Layer Security (TLS), and Secure Shell (SSH). Embodiments may implement any desired application layer protocol, including http, https, ftp, and sftp.

The various system components may be independently, separately or collectively suitably coupled to a network via data links which includes, for example, a connection to an Internet Service Provider (ISP) over the local loop as is typically used in connection with standard modem communication, cable modem, satellite networks, ISDN, Digital Subscriber Line (DSL), or various wireless communication methods. It is noted that embodiments of the present disclosure may operate in conjunction with any suitable type of network, such as an interactive television (ITV) network.

The system may be partially or fully implemented using cloud computing. "Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

Various embodiments may be used in conjunction with web services, utility computing, pervasive and individualized computing, security and identity solutions, autonomic computing, cloud computing, commodity computing, mobility and wireless solutions, open source, biometrics, grid computing and/or mesh computing.

Any databases discussed herein may include relational, hierarchical, graphical, or object-oriented structure and/or any other database configurations. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically.

Any databases, systems, devices, servers or other components of the system may be located at a single location or at multiple locations, wherein each database or system includes any of various suitable security features, such as firewalls, access codes, encryption, decryption, compression, decompression, and/or the like.

Encryption may be performed by way of any of the techniques now available in the art or which may become available—e.g., Twofish, RSA, El Gamal, Schorr signature, DSA, PGP, PKI, and symmetric and asymmetric cryptosystems.

Embodiments may connect to the Internet or an intranet using standard dial-up, cable, DSL or any other Internet protocol known in the art. Transactions may pass through a firewall in order to prevent unauthorized access from users of other networks.

The computers discussed herein may provide a suitable website or other Internet-based graphical user interface which is accessible by users. For example, the Microsoft Internet Information Server (IIS), Microsoft Transaction Server (MTS), and Microsoft SQL Server, may be used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system. In another example, an Apache web server can be used in conjunction with a Linux operating system, a MySQL database, and the Perl, PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), AJAX (Asynchronous Javascript And XML), helper applications, plug-ins, and the like. A server may include a web service that receives a request from a web server, the request including a URL and an IP address. The web server retrieves the appropriate web pages and sends the data or applications for the web pages to the IP address. Web services are applications that are capable of interacting with other applications over a communications means, such as the Internet.

Various embodiments may employ any desired number of methods for displaying data within a browser-based document. For example, data may be represented as standard text or within a fixed list, scrollable list, drop-down list, editable text field, fixed text field, pop-up window, and the like. Likewise, embodiments may utilize any desired number of methods for modifying data in a web page such as, for example, free text entry using a keyboard, selection of menu items, check boxes, option boxes, and the like.

The exemplary systems and methods illustrated herein may be described in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, VBScript, Macromedia Cold Fusion, COBOL, Microsoft Active Server Pages, assembly, PERL, PHP, AWK, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like.

The systems and methods of the present disclosure may be embodied as a customization of an existing system, an add-on product, a processing apparatus executing upgraded software, a stand alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" should be construed to exclude only those types of transitory computer-readable media which were found in *In Re Nuijten* to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure.

Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Changes and modifications may be made to the disclosed embodiments without departing from the scope of the present invention. These and other changes or modifications are intended to be included within the scope of the present disclosure, as expressed in the following claims.

What is claimed is:

1. A computer-implemented method comprising:
   receiving, by a computer system, sensor data related to motion by an actor over a time period;
   determining a local vertical vector for the actor for use in determining an angle of self-rotation for the actor and an angle of flip for the actor, the determining the local vertical vector based on sensor data from one or more magnetometers;
   determining, by the computer system and based on the sensor data, a plurality of motion characteristics including determining the angle of self-rotation for the actor and determining the angle of flip for the actor,
   wherein determining the angle of self-rotation for the actor includes:
      calculating a plurality of unit vectors orthogonal to the local vertical vector for the actor;
      calculating a plurality of angles determining rotation of the unit vectors around the local vertical vector; and
      selecting the angle of self-rotation for the actor as a maximum angle from the plurality of angles;
   receiving a plurality of athletic maneuver definitions, wherein each athletic maneuver definition comprises a set of motion characteristics associated with athletic maneuvers;
   identifying an athletic maneuver definition from the plurality of athletic maneuver definitions, wherein identifying an athletic maneuver definition from the plurality of athletic maneuver definitions comprises selecting an athletic maneuver definition having a set of motion characteristics that includes the determined angle of self-rotation for the actor and the determined angle of flip for the actor; and
   overlaying information related to the athletic maneuver on video of the actor performing the athletic maneuver, wherein the information related to the athletic maneuver is at least based on the determined angle of self-rotation for the actor and the determined angle of flip for the actor.

2. The method of claim 1, wherein the plurality of motion characteristics includes one or more of: position; velocity; acceleration; orientation; rotation; and translation.

3. The method of claim 1, wherein the sensor data includes data from one or more of: an accelerometer; a gyroscope; a magnetometer; a Hall effect sensor; a global positioning system; an ultrasonic sensor; and an optical sensor.

4. The method of claim 1, wherein at least one of the plurality of motion characteristics is determined relative to one or more axis of an absolute frame of reference that is independent of the actor, and wherein at least one other of the plurality of motion characteristics is determined relative to one or more axis of a local frame of reference that is associated with the actor.

5. The method of claim 1, wherein determining the plurality of motion characteristics includes determining an orientation for the actor at the beginning of the time period.

6. The method of claim 1, wherein determining the plurality of motion characteristics includes determining a facing for the actor based on a direction of a velocity vector calculated from the sensor data and a direction of a magnetic vector calculated using information from a magnetometer sensor in the sensor data.

7. The method of claim 1, wherein identifying the athletic maneuver includes comparing the plurality of determined motion characteristics to one or more motion characteristics associated with a known athletic maneuver.

8. The method of claim 1, further comprising:
   determining the quality of the determined motion characteristics, wherein the quality of the determined motion characteristics is determined based on a level of similarity between each of the determined motion characteristics and each of the motion characteristics associated with the identified athletic maneuver; and
   generating an alert in response to the level of similarity being beneath a predetermined threshold.

9. The method of claim 7, wherein the one or more motion characteristics associated with the known athletic maneuver includes one or more of:
   an orientation of the actor at a start of the time period;
   an angle of rotation around a local axis of the actor;
   a direction of rotation of the actor around a local axis of the actor;
   an angle of rotation around an absolute axis perpendicular to a plane of motion of the actor;
   a direction of rotation round an absolute axis perpendicular to a plane of motion of the actor; and
   a leading edge of a piece of sports equipment at a start of the time period.

10. The method of claim 7, wherein the known athletic maneuver is stored in the database with one or more associated motion characteristics.

11. A non-transitory, computer-readable medium storing instructions that, when executed, cause a computing device to:
- receive sensor data related to motion by an actor over a time period;
- determine a local vertical vector for the actor for use in determining an angle of self-rotation for the actor and an angle of flip for the actor, the determining the local vertical vector based on sensor data from one or more magnetometers;
- determine, based on the sensor data, a plurality of motion characteristics including determining the angle of self-rotation for the actor and determining the angle of flip for the actor,
  - wherein determining the angle of self-rotation for the actor includes:
    - calculating a plurality of unit vectors orthogonal to the local vertical vector for the actor;
    - calculating a plurality of angles determining rotation of the unit vectors around the local vertical vector; and
    - selecting the angle of self-rotation for the actor as a maximum angle from the plurality of angles;
- receive a plurality of athletic maneuver definitions, wherein each athletic maneuver definition comprises a set of motion characteristics associated with athletic maneuvers;
- identify an athletic maneuver definition from the plurality of athletic maneuver definitions, wherein identifying an athletic maneuver definition from the plurality of athletic maneuver definitions comprises selecting an athletic maneuver definition having a set of motion characteristics that includes the determined angle of self-rotation for the actor and the determined angle of flip for the actor; and
- overlay information related to the athletic maneuver on video of the actor performing the athletic maneuver, wherein the information related to the athletic maneuver is at least based on the determined angle of self-rotation for the actor and the determined angle of flip for the actor.

12. A system comprising:
at least one processor; and
memory in communication with the at least one processor and storing instructions that, when executed by the processor, cause the system to:
- receive sensor data related to motion by an actor over a time period;
- determine a local vertical vector for the actor for use in determining an angle of self-rotation for the actor and an angle of flip for the actor, the determining the local vertical vector based on sensor data from one or more magnetometers;
- determine, based on the sensor data, a plurality of motion characteristics including determining the angle of self-rotation for the actor and determining the angle of flip for the actor,
  - wherein determining the angle of self-rotation for the actor includes:
    - calculating a plurality of unit vectors orthogonal to the local vertical vector for the actor;
    - calculating a plurality of angles determining rotation of the unit vectors around the local vertical vector; and
    - selecting the angle of self-rotation for the actor as a maximum angle from the plurality of angles;
- receive a plurality of athletic maneuver definitions, wherein each athletic maneuver definition comprises a set of motion characteristics associated with athletic maneuvers;
- identify an athletic maneuver definition from the plurality of athletic maneuver definitions, wherein identifying an athletic maneuver definition from the plurality of athletic maneuver definitions comprises selecting an athletic maneuver definition having a set of motion characteristics that includes the determined angle of self-rotation for the actor and the determined angle of flip for the actor; and
- overlay information related to the athletic maneuver on video of the actor performing the athletic maneuver, wherein the information related to the athletic maneuver is at least based on the determined angle of self-rotation for the actor and the determined angle of flip for the actor.

13. The method of claim 1, wherein the time period is measured from a global positioning system, based on a signal from a gyroscope or based on fuzzy logic analysis of one or more sensor signals.

14. The method of claim 1, wherein the determining the local vertical vector is further based on one or more of:
- an average of sensor data from one or more accelerometers prior to an athletic maneuver that occurs during the time period;
- an average of sensor data from one or more accelerometers after the athletic maneuver; and
- sensor data from one or more accelerometers associated with a portion of the athletic maneuver.

15. The method of claim 14, wherein determining the angle of flip for the actor includes:
- determining motion of the local vertical vector, associated with the actor, in a global frame of reference;
- identifying a plane of movement for the vertical unit vector based of the motion of the local vertical vector;
- calculating a projection of the local vertical vector on the plane; and
- selecting the angle of flip for the actor as the angle of an arc segment traveled by the projection on the plane.

16. The method of claim 1, wherein determining the angle of flip for the actor includes:
- determining motion of the local vertical vector, associated with the actor, in a global frame of reference;
- identifying a plane of movement for the vertical unit vector based of the motion of the local vertical vector;
- calculating a projection of the local vertical vector on the plane; and
- selecting the angle of flip for the actor as the angle of an arc segment traveled by the projection on the plane.

17. The non-transitory computer-readable medium of claim 11, wherein the determining the local vertical vector is further based on one or more of:
- an average of sensor data from one or more accelerometers prior to an athletic maneuver that occurs during the time period;
- an average of sensor data from one or more accelerometers after the athletic maneuver; and
- sensor data from one or more accelerometers associated with a portion of the athletic maneuver.

18. The non-transitory computer-readable medium of claim 17, wherein determining the angle of flip for the actor includes:
- determining motion of the local vertical vector, associated with the actor, in a global frame of reference;

identifying a plane of movement for the vertical unit vector based of the motion of the local vertical vector;

calculating a projection of the local vertical vector on the plane; and selecting the angle of flip for the actor as the angle of an arc segment traveled by the projection on the plane.

19. The system of claim 12, wherein the determining the local vertical vector is further based on one or more of:

an average of sensor data from one or more accelerometers prior to an athletic maneuver that occurs during the time period;

an average of sensor data from one or more accelerometers after the athletic maneuver; and sensor data from one or more accelerometers associated with a portion of the athletic maneuver.

20. The system of claim 19, wherein determining the angle of flip for the actor includes:

determining motion of the local vertical vector, associated with the actor, in a global frame of reference;

identifying a plane of movement for the vertical unit vector based of the motion of the local vertical vector;

calculating a projection of the local vertical vector on the plane; and selecting the angle of flip for the actor as the angle of an arc segment traveled by the projection on the plane.

* * * * *